United States Patent
Xia et al.

(10) Patent No.: US 9,808,429 B2
(45) Date of Patent: Nov. 7, 2017

(54) TOPICAL DRUG PATCH INCLUDING MICROSPHERES

(71) Applicant: Swansea University, Swansea (GB)

(72) Inventors: Zhidao Xia, Swansea (GB); Alan Marsh, Swansea (GB)

(73) Assignee: Swansea University, Swansea (GB)

( * ) Notice: Subject to any disclaimer, the term of this patent is extended or adjusted under 35 U.S.C. 154(b) by 0 days.

(21) Appl. No.: 14/913,540

(22) PCT Filed: Aug. 18, 2014

(86) PCT No.: PCT/GB2014/000322
§ 371 (c)(1),
(2) Date: Feb. 22, 2016

(87) PCT Pub. No.: WO2015/025119
PCT Pub. Date: Feb. 26, 2015

(65) Prior Publication Data
US 2016/0199314 A1 Jul. 14, 2016

(30) Foreign Application Priority Data
Aug. 21, 2013 (GB) .................................. 1314909.1

(51) Int. Cl.
*A61K 9/70* (2006.01)
*A61K 9/50* (2006.01)
*A61K 31/593* (2006.01)
*A61K 31/122* (2006.01)
*A61F 13/02* (2006.01)

(52) U.S. Cl.
CPC ............ *A61K 9/703* (2013.01); *A61K 9/5031* (2013.01); *A61K 9/7092* (2013.01); *A61K 31/122* (2013.01); *A61K 31/593* (2013.01); *A61F 13/0259* (2013.01)

(58) Field of Classification Search
None
See application file for complete search history.

(56) References Cited

U.S. PATENT DOCUMENTS

| 2003/0175328 A1* | 9/2003 | Shefer | A61K 8/0208 424/449 |
| 2006/0083778 A1* | 4/2006 | Allison | A61K 9/145 424/448 |
| 2007/0224254 A1* | 9/2007 | Yu | A61K 9/5057 424/449 |
| 2010/0291191 A1* | 11/2010 | Shoichet | A61K 9/0024 424/450 |

FOREIGN PATENT DOCUMENTS

| EP | 0739626 A2 | 10/1996 |
| WO | 2004019920 A1 | 3/2004 |

OTHER PUBLICATIONS

International Search Report from co-pending international application No. PCT/GB2014/000322, dated Nov. 28, 2014.

* cited by examiner

*Primary Examiner* — Robert A Wax
*Assistant Examiner* — Quanglong Truong
(74) *Attorney, Agent, or Firm* — Dinsmore & Shohl LLP

(57) ABSTRACT

A topical drug delivery patch (1) comprising a drug delivery layer (3) including microspheres (2) encapsulating a drug, said microspheres being carried in a hydro gel. The drug delivery layer has a support layer (5) which is attached to a first face of the drug deliver layer and a releasable protective layer (4) attached to a second face of the drug delivery layer. The releasable protective layer can be peeled away do the patch can be applied to the skin to release drugs in the microspheres. The patch is particularly useful for treating skin conditions such as psoriasis and eczema.

16 Claims, 3 Drawing Sheets

TOPICAL DRUG PATCH INCLUDING MICROSPHERES

FIELD OF THE INVENTION

The present invention relates to topical drug delivery device including microspheres. In particular but not exclusively the topical drug delivery device is in the form of a hydrogel patch having microspheres including drugs for the treatment of dermal conditions.

BACKGROUND OF THE INVENTION

Drug delivery refers to the method, formulation and technology for carrying a pharmaceutical compound to a specific site of action in the body. A drug delivery system can consist of a drug working in combination with a medical device, or it could only be a chemical formulation of a drug.

Different methods of drug administration have been designed to supplement the large number of new drugs being produced and to support those that can't be delivered by oral ingestion or injection. Oral drug administration is not always highly reliable due to a tendency to have negligible or very little absorption due to enzymatic degradation in the gastro-intestinal tract and liver. Also, for example in the case of Aspirin if taken orally, in high doses, it causes gastrointestinal ulcers. The routes of pharmaceutical delivery are usually determined by the disease that needs to be treated and the kind of effect the drug needs to have and a drug is usually administered systemically or directly to the target site.

One particular method of applying a drug to a patient that has shown much promise, is using a transdermal patch. This allows the drug to pass through or into the skin for a variety of potential treatments. However, often it is difficult for the majority of a drug to pass through the skin at therapeutically useful rates thus far. This is due to the outer stratum corneum layer of the skin acting as a natural barrier to external infiltration so making transdermal drug delivery very limited.

Particularly difficult conditions to treat are skin conditions such as eczema and psoriasis. The real cause of psoriasis still not fully understood; however there are two ideas about how this disorder develops. The first hypothesis indicates that Psoriasis is an immune-mediated disorder in which affecting the excessive reproduction of the skin cells. The second hypothesis indicates that Psoriasis is due to dysfunction of the epidermis and keratinocytes, which is, then cause to excessive growth and reproduction of the skin cells.

Symptoms of Psoriasis differ from one type to other, but the general symptoms would be inflammation, erythema (redness), thickness, heat and scaling. Patient suffering Psoriasis reported that they have significant feeling of self-consciousness and embarrassment and they usually avoided social activities and limited dating or friendly interactions.

Currently there are no absolute cures for this disease; however there are different treatments methods, which could help to control the symptoms such as using topical creams, gels and ointment formulations relieve the inflammation and slow down the reproduction of the skin cells. The problem with these methods is they could spread on the healthy part of the skin, dying them, due to the yellow colour of drug and cause irritation. The dose also cannot be consistent per $cm^2$ due to applying inconsistently by patients.

Accordingly, there is a continued interest therefore in the development of new topical compositions that could efficiently treat a subject suffering from the above condition.

The present invention seeks to overcome problems associated with the prior art by providing a delivery system that can be applied to the skin and which releases drugs to the skin at a therapeutically acceptable level. The drug delivery device of the invention is particularly useful for treating long term debilitating skin diseases such as eczema and psoriasis where targeted delivery is required over a period of time, while avoiding irritating the skin or causing the disease to spread further.

SUMMARY OF THE INVENTION

According to a first aspect of the present invention there is provided a topical drug delivery patch comprising a drug delivery layer including microspheres encapsulating a drug, said microspheres being carried in a hydrogel, said drug delivery layer having a support layer which is attached to a first face of the drug deliver layer and a releasable protective layer attached to a second face of the drug delivery layer, with the releasable protective layer being removable such that in use the second face can be applied to the skin of an individual so the drug in the microspheres can be released onto the skin while the support layer forms a covering for the drug delivery layer.

Preferably the microspheres are oil based.

It is envisaged that the microspheres are formed from polycaprolactone (PCL), polylactide-co-glycolide acid (PLGA) or a combination thereof.

It is preferred that the microspheres are biodegradable.

It is envisaged that the hydrogel is a hydrophilic material.

Preferably the hydrogel is an adhesive gel composition containing a water-soluble polymer gel, water and water holding agent.

Preferably the microspheres encapsulate one or more drugs for treating skin conditions.

It is preferred that at least one of the one or more drugs is oil-based.

Preferably the one or more oil-based drugs are selected from one or more of dithranol or calcipotriol.

It is envisaged that the drug-encapsulated microspheres and hydrogel are mixed at a ratio of 1 to 20% (w/w).

It is preferred that the majority of microspheres have a diameter of between 80 and 250 microns, more particularly 90 to 220 microns and more particularly 100 to 200 microns.

It is preferred that the hydrogel contains drug encapsulated microspheres throughout the hydrogel with a greater concentration being situated towards the second face of the drug delivery layer.

According to a further aspect of the invention there is provided a kit including a topical drug delivery patch comprising a drug delivery layer microspheres carried in a hydrogel, said drug delivery layer having a support layer which is attached to a first face of the drug deliver layer and a releasable protective layer attached to a second face of the drug delivery layer, wherein the releasable protective layer can be removed so that the second face can be applied to the skin of an individual while the support layer forms a covering for the drug delivery layer the kit further including a sheet of material that can be cut to provide a template for cutting the topical drug delivery patch into a desired shape for affixing to the individual.

It is envisaged that the topical drug delivery patch or the kit including the topical drug delivery patch is adapted for the treatment of a skin condition.

Preferably the skin condition is psoriasis or eczema or a combination thereof.

BRIEF DESCRIPTION OF THE DRAWINGS

An embodiment of the invention will now be described by way of example only with reference to and as illustrated in the following figures and examples in which.

DETAILED DESCRIPTION OF AN EMBODIMENT OF THE INVENTION

Figure 1:
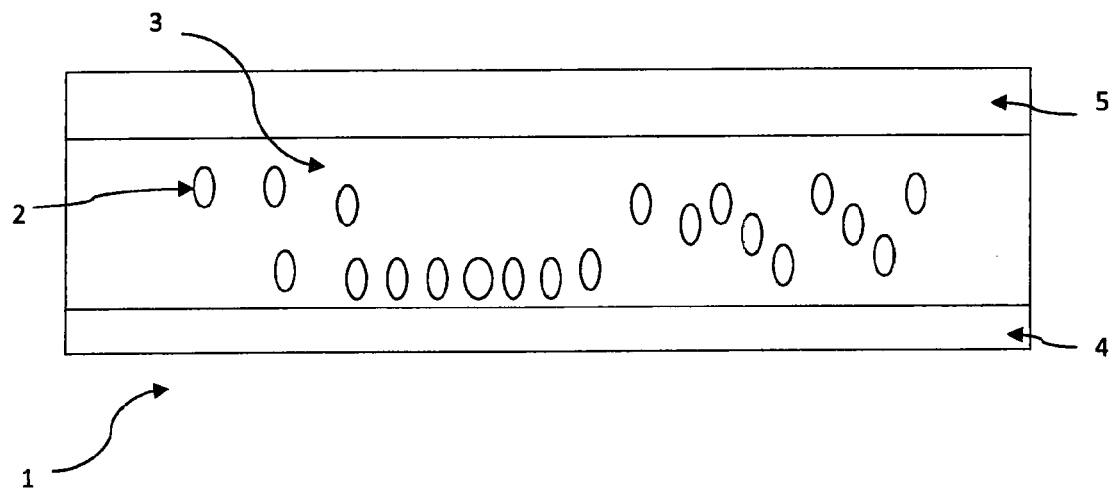
FIG. 1 shows: a cross section of a drug delivery patch according to an embodiment of the invention.
Figure 2:
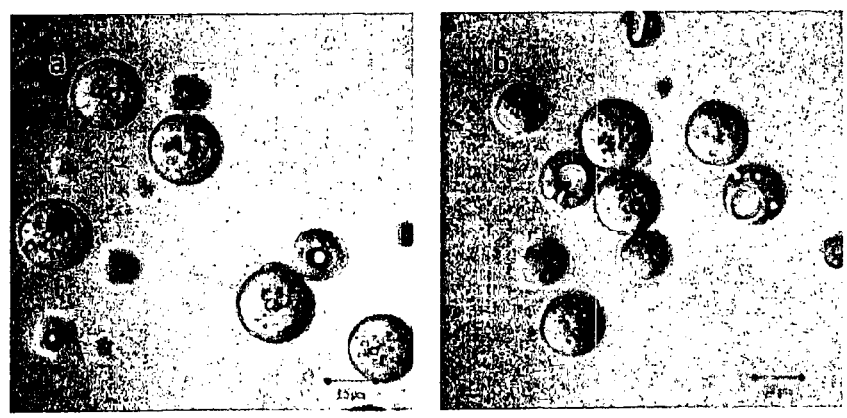
FIG. 2 shows: a bright field image of Dithranol encapsulated PLGA microsphere.

The present invention relates to topical, drug-loaded polymer microspheres which are incorporated in or on a hydrogel patch. The patches, which are generally shown as 1 in FIG. 1, consist of oil-based, drug-loaded microspheres 2, contained in a hydrogel 3. The hydrogel can be based on an adhesive gel composition containing a water-soluble polymer gel, water and water holding agent. The hydrogel layer has two faces, a first face which is covered by a support layer 5 and a second face that is on the opposite face of the hydrogel layer to the first which is covered by a protective layer 4. The support layer 5 forms a barrier to damage to the hydrogel and keeps the hydrogel clean and dry. The barrier layer may even be coloured to match the skin tone of the individual or it may be patterned to form body adornment. The protective sheet 4 that can be peeled away from the face of the hydrogel so it can be applied to the skin. The microspheres are heated by the body of the individual and so drug in the microspheres is released to the skin of the individual. It is desirable that there are more microspheres in the gel in the area closest to the protective layer 4 so that there can be an initial treatment followed by sustained treatment in by microspheres that are more remote from the first face as the microspheres can release drug to the skin, which may be as a result of the microspheres melting if a thermosensitive material is used. In particular the patches are applied to a subject with a skin condition and remain on the applied area for a period of time that is sufficient for an effective dose of the oil-based drug to be released onto the skin surface that is in direct contact with patch containing the microspheres. This invention can be used for treatment of a variety of skin conditions which require the application of oil-based drugs.

The oil-based drugs are encapsulated in polymer microspheres. The said oil-based drugs are dithranol, calcipotriol, or any oil-based active ingredients which are able to treat skin conditions.

The polymer microspheres are produced from biomaterials. Such biomaterials include synthetic biodegradable polymers formed of hydrophobic material e.g. the a -hydroxy acids family including Polycaprolactone (PCL) Polymer, poly lacto-co-glycolic acid (PLGA) and polyanhydrides and also naturally occurring polymers, for example complex sugars such as chitosan and hyaluronan, and inorganic ones such as hydroxyapatite.

PCL is a biocompatible and biodegradable polymer with semicrystalline structure and very low glass transition temperature. PCL is suitable for long-term delivery action as it has very slow degradation over period of time. The semicrystalline PCL polymer has a glass transition temperature of 60° C. and the range of melting point between 59 and 64° C., which is, depend on its crystalline nature of PCL. The average molecular weight of this polymer is varying from 10,000 to 42,500 and it is soluble in Dichloromethane, Chloroform, Carbon tetrachloride, Toluene, Benzene, 2-nitropropane and Cyclohexanone at room temperature. This polymer has low solubility in Ethyl acetate, Acetone, 2-butanone, Dimethylformamide and acetonitrile and it is insoluble in petroleum ether, diethyl ether and alcohol. Polycaprolactone can be blended with other polymers, to improve dyeability, adhesion and stress crack resistance. It could combine with polymers such as cellulose acetate butyrate, cellulose propionate, polylactic acid and polylactic acid-co-glycolic acid, for manipulating the drug release rate from microspheres.

PLGA is again a biocompatible polymer. There are many factors that influence in physical property of PLGA. These factors include the ratio of lactide to glycolide, initial molecular weight, size of the device, storage temperature and exposure to water. Polydispersity index and molecular index are two physical properties factors that affect the mechanical strength of the PLGA. These properties also affect the formulation of PLGA to be use as a drug delivery device and it could also affect the rate of degradation and hydrolysis. The degree of the crystallinity of PLGA reduced when crystalline PGA co-polymerized with PLA and then it would increase the hydration and hydrolysis rate. Further degradation rate of the PLGA depend on the ratio of PGA to PLA. The fastest degradation belongs to 50:50 ratio of PLA to PGA (as an exception). However as a rule, the higher PGA content leads to faster degradation rate.

Biodegradation of PLGA copolymers could take place via hydrolysis or degradation through cleavage of its ester linkage backbone into oligomers and then monomers. The process of degradation is mainly via uniform bulk degradation of the matrix in which the polymer degradation rate is less than water penetration into the matrix. Additionally the increase of carboxylic end groups autocatalysis the process of degradation. The collective process of diffusion and erosion of bulk and surface determine the degradation of PLGA copolymers. The release rate is unpredictable as there are many variables that affect the process of degradation. Further the rate of degradation of the PLGA copolymers is reliant on different factors including molecular weight of the polymer, crystallinity degree rate, molar ratio of the Glycolic to lactic acids, and glass transition temperature of the polymer.

For drug encapsulation, 200 mg PCL is dissolved into 4 ml chloroform. 5 ml of 1mg/1ml dithranol is added into the PCL-chloroform mixture, and continued to mix in a homogenizer device for 1 or 2 minutes to reach an even distribution. 9 ml drug-PCL-chloroform is injected into a variety concentration of PVA solution with a syringe under a magnetic stirrer at around 100 rmp. The mixture was left to stir for at least 4 hours in a fume cabinet to make sure that the spheres nicely formed and solidified, and to allow full evaporation of chloroform from the mixture. A variety of sieves between 1 and 500 micrometer could be use to collect the particular size of the microspheres. This part could be takes place if there is need to avoid large range of size of microspheres. The microspheres are washed in deionised water and pelleted using centrifugation, and freezing dried for storage before hydrogel patch preparation. Certain size range of the drug encapsulated microspheres can be tuned by altering the concentration of Poly Vinyl Alcohol (PVA). The morphology of the microspheres are observed by bright field microscopy and scanning electron microsocopy (SEM). The size of the microspheres is measured using a Malvern Mastersizer 2000. 18 g of PVA mixed with 1800 ml of deionised water with heating. It was stirred on the hot-plate stirrer until it fully dissolved and gives the 1% w/v solution. The temperature was around 70 degree Celsius.

A number of techniques are used to quantify the encapsulated drugs in microspheres, these include using thin layer chromatography (TCL), UV spectrometry and mass-spectra. The encapsulation rate of the drugs was calculated by measured drug loading to given weight of microspheres over the actual drug loaded to the microspheres. The calculated drug loading rate is reached 100%.

Encapsulation of drugs inside the microspheres rather than loading them into the gel has several advantages. The microspheres protect the drugs prior to delivery, for example from desiccation whilst allowing the drug to be easily transferred to the site of action when required in a controlled manner over certain period of time so allowing control of the dose and toxicity.

Drug encapsulated microspheres are mixed with hydrogel to form microspheres-hydrogel patch. The microspheres are either partially or completely embedded into hydrogel. These patches, once formed are expected for clinical application after systemic assessment. Hydrogels are composed of a network of hydrophilic polymer chains. They may be a colloidal gel with water as the dispersion medium. Hydrogels contain more than 99.9% water making them highly absorbent to synthetic or natural polymer. Because of the significant water content, the hydrogels have a flexibility that is very similar to natural tissues. The hydrogel patches include an adhesive hydrogel on a carrier base, which can be directly applied to the skin surface. The hydrogel patch can be loaded so as to provide a consistent dose per cm² when compared with other topical applications such as creams, gels or ointments which are often applied so as to have inconsistent coverage of the skin. In addition hydrogel patches have the advantage that they can be cut to a particular shape to be positioned on a patient's skin and by cutting the patch to a particular shape, the dose is only applied to the site of the skin problem—rather than the healthy tissue surrounding it—thereby lessening any possible adverse effects of the drugs.

As part of a package for a delivery system a sheet of material such as plastic may be supplied with the hydrogel patch and this sheet is suitable for cutting into the shape matching, for example an area of the skin of the patient that needs treatment. This individually shaped piece of plastic could then act as a template for cutting future patches into the correct shape if repeated treatment of an area of skin is required.

The patches are applied and held on the skin with adhesive and typically a low tack adhesive is used that allows the patch to be gently applied and removed from the skin. Using a gentle adhesive is especially important for dermatological conditions where the skin is usually already damaged or liable to damage, inflammation, or loss of skin integrity. The patches are also ideally made of a material that has some give or stretchability to allow the patches to stretch and conform to skin as it moves therefore lessening any possible mechanical damage compared to less flexible patch technology.

The microspheres are based on components that are generally recognised as being safe in the pharmaceutical filed. The microspheres allow for a reservoir of the active ingredient to build up in the skin layers—where the pharmacological action is required—without significant penetration through the skin leading to undesirable systemic allergic reactions. The microspheres provide a controlled release of agent so that a drug can be applied over a longer period of time which means that applications are only needed once or twice per day as compared with an ointment which often needs several applications per day due to the ointment being washed or rubbed away. Using a patch is also considerably less "messy" than conventional creams, gels or ointments in the topical application process.

The hydrogels are used in conjugation with drug carriers as part of a sustained release delivery system. Typically the drug carriers are needed because the drugs that are carried (being oil based) are insoluble in water. The hydrogels are protected by a protective layer that can be peeled off the hydrogel so the hydrogel can be applied to the skin. The hydrogel itself can include an adhesive or have an outer stratum that includes an adhesive, which preferably is low tack so that there is gentle adhesion which is especially important for dermatological conditions—where the skin is usually already damaged or liable to damage, inflammation, or loss of skin integrity. Also these patches will stretch and conform to skin as it moves, therefore lessening any possible mechanical damage compared to less flexible patch technology The patch is aimed at a targeted delivery of a drug in which the drug is only active in a specific area of the body and perhaps, under specific conditions. This system has to maintain rate of release, ensuring the drug is released in a controlled manner over a period of time. The drug delivery device of the present invention is designed to keep the drug on the skin surface, as opposed to being able to pass through it. This lends itself perfectly to the treatment of various skin diseases such as Psoriasis or Eczema.

FIGS. 2 shows bright field images using a confocal microscope of Dithranol encapsulated PLGA microspheres and it is interesting that there are crystalize formation appear inside each sphere which may be due to encapsulation of the drug having an influence on the spheres. There may be a range of size of the microspheres. Generally microspheres tend to have smooth non-porous bulk structure; however there may be streaky and non-uniform surface morphology due to actions such as freeze-drying which may cause the microsphere surface to shrink.

Studies have been conducted using a Mattersizer 2000, and it was found that the mean particle size of non-porous PLGA microspheres was about 70 micron. Particles synthesised in 0.01 mg/ml concentration of PVA. Studies were also carried out using non-porous PCL microspheres with different concentration of Poly Vinyl Alcohol (PVA) and it was found for the average of 10 tests run using a Mattersizer 200 on each sample that the mean particle size for a first sample was 106.733 micron, for a second sample it was 121.781 micron and for a third sample it was found to be about 171.514 microns. The concentration of PVA appears to have an effect on the size of the microspheres and it appears that as the concentration of the PVA decreases, the size of the particles gets larger. The PVA concentration in sample 1 was 0.01 mg/ml, in sample 2 it was 0.005 mg/ml and in sample 3 it even more decreased to 0.003 mg/ml. Studies have found that the majority of microspheres were around 100 to 200 microns in diameter with the surface area of the particles was from 0.055 metres square per gram to 0.034 meters square per gram.

It would appear from the studies carried out that in general PCL microspheres appear to be slightly larger than PLGA microspheres.

Figure 3:
FIG. 3 shows: SEM images of Dithranol encapsulated microspheres where the spheres are non-porous and have smooth outer shell.
Figure 4:
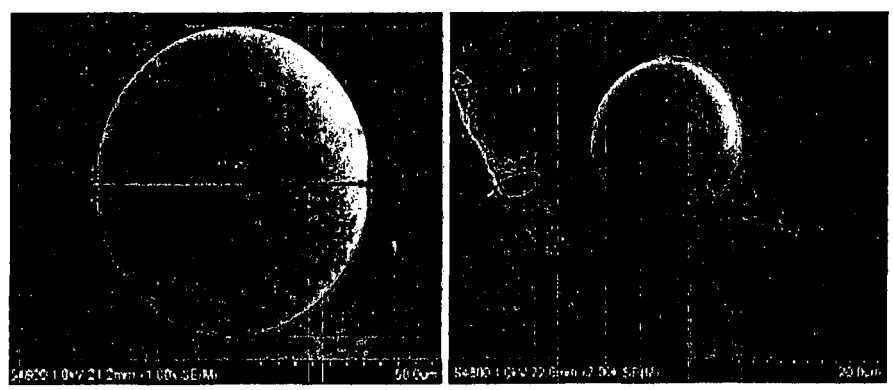
FIG. 4 shows: SEM images of the Calcipotriol encapsulated microspheres having a non-porous and smooth outer shell.

FIG. 3 shows SEM images of Dithranol encapsulated microspheres, while FIG. 4 shows SEM images of the Calcipotriol encapsulated microspheres and in both instances the microspheres have a non-porous and smooth outer shell.

Figure 5:
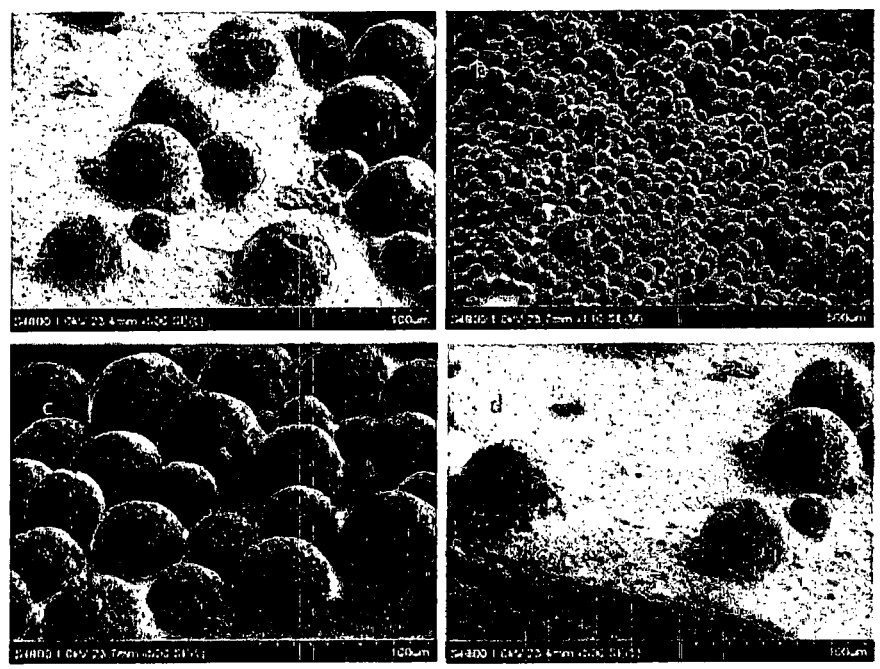
FIG. 5 shows: SEM image of PCL microspheres embedded in the hydrogel patch.

FIG. 5 shows SEM image of PCL microspheres embedded in the hydrogel patch. Higher magnification of the images shows the adhesive gel caused the microspheres to adhere. The image with lower magnification on the left hand side bottom shows how the microspheres dispersed through the hydrogel, some of them embedded and some of them just attached on the surface.

To embed PCL microspheres in the hydrogel a batch of fresh PCL microspheres with loaded drug was synthesised. The microspheres then freeze dried over night. The plastic membrane on the top of the hydrogel patch was removed and the freeze dried microspheres then were sprayed on the top of the hydrogel patch. The membrane was placed back of the top of the gel and the sprayed microspheres then pressed slightly into the gel to make sure that the microspheres adhered enough to the gel. The membrane was removed again and the sample was taken bright field imaging and SEM analysis.

When the patch is applied to the skin there is an initial burst of drug release due to release of drug at the surface of the hydrogel and hydrophobicity of polymer. Any drug on the surface of the polymer, which is in contact with the medium, is released due to solubility function and penetration of water into the polymer matrix. In the second phase, drug is progressively released through the outer layer and it is completely depleted of drug. The water that entered the surface layer hydrolyses the polymer into oligomeric and monomeric products. This is help drug to be released by diffusion and erosion until complete solubilisation of the polymer.

As can be seen, the present invention provides a sustained release patch that can deliver an initial amount of drug to a targeted area while thereafter providing sustained release of that drug. In particular the patch is easy to apply to a much targeted area of the skin so that topical delivery of drugs can be provided for the treatment of skin diseases such as psoriasis.

It should be noted that the above mentioned embodiment illustrates rather than limits the invention and that alterations or modifications are possible without departing from the scope of the invention as described. It is to be noted that the invention covers not only individual embodiments described but also combinations of those embodiments. It will be apparent to those of ordinary skill in the art that various modifications and equivalents can be made without departing from the spirit and scope of the invention.

The invention claimed is:

1. A topical drug delivery patch, comprising:
    a hydrogel;
    a drug delivery layer including the hydrogel and microspheres encapsulating a drug, said microspheres being carried in the hydrogel, the microspheres each formed of a solid polymer having the drug encapsulated therein;
    a support layer which is attached to a first face of the drug deliver layer; and
    a releasable protective layer attached to a second face of the drug delivery layer, with the releasable protective layer being removable such that in use the second face can be applied to the skin of an individual so the drug in the microspheres can be released onto the skin while the support layer forms a covering for the drug delivery layer.

2. A topical drug delivery patch according to claim 1, wherein the microspheres are oil based.

3. A topical drug delivery patch according to claim 1 wherein the microspheres are formed from polycaprolactone (PCL), polylactide-co-glycolide acid (PLGA) or a combination thereof.

4. A topical drug delivery patch according to claim 1 wherein the microspheres are biodegradable.

5. A topical drug delivery patch according to claim 1 wherein the hydrogel is a hydrophilic material.

6. A topical drug delivery patch according to claim 5, wherein the hydrogel is an adhesive gel composition containing a water-soluble polymer gel, water and water holding agent.

7. A topical drug delivery patch according to claim 1 wherein the microspheres encapsulate one or more drugs for treating skin conditions.

8. A topical drug delivery patch according to claim 7 wherein at least one of the one or more drugs is oil-based.

9. A topical drug delivery patch according to claim 8, wherein the one or more oil-based drugs are selected from one or more of dithranol or calcipotriol.

10. A topical drug delivery patch according to claim 1 wherein the drug- encapsulated microspheres and hydrogel are mixed at a ratio of 1 to 20% (w/w).

11. A topical drug delivery patch according to claim 1 wherein the majority of microspheres have a diameter of between 80 and 250 microns, more particularly 90 to 220 microns and more particularly 100 to 200 microns.

12. A topical drug delivery patch according to claim 1 wherein the hydrogel contains drug encapsulated microspheres throughout the hydrogel with a greater concentration being situated towards the second face of the drug delivery layer.

13. A kit including a topical drug delivery patch according to claim 1 wherein the kit further includes a sheet of material that can be cut to provide a template for cutting the topical drug delivery patch into a desired shape for affixing to the individual.

14. A topical drug delivery patch according to claim 1, wherein the topical drug delivery patch is adapted for the treatment of a skin condition.

15. A topical drug delivery patch according to claim 14, wherein the skin condition is psoriasis or eczema or a combination thereof.

16. A topical drug delivery patch according to claim 1, wherein the microspheres are more concentrated near the second face.

* * * * *